United States Patent [19]

Brufani et al.

[11] Patent Number: 5,378,844
[45] Date of Patent: Jan. 3, 1995

[54] 8-(1-AMINOCYCLOALKYL)-1,3-DIALKYLXANTHINE DERIVATIVES, PREPARATION PROCESS AND ANTIDEPRESSANT, NOOTROPIC AND PSYCHOSTIMULANT COMPOSITION THEREOFF

[75] Inventors: Mario Brufani, Rome; Romolo Scuri, Piacenza; Stefano Ceccarelli, Frosinone; Patrizia DeVellis, Frosinone; Patrizia Giannetti, Frosinone; Agnese Paesano, Frosinone; Zanarella Sergio, Mentana, all of Italy

[73] Assignee: Biomedica Foscama Industria Chimico-Farmaceutica S.p.A., Rome, Italy

[21] Appl. No.: 7,757

[22] Filed: Jan. 22, 1993

[30] Foreign Application Priority Data

Jan. 24, 1992 [IT] Italy ............... MI91 A 000132

[51] Int. Cl.⁶ ............................................. C07D 473/08
[52] U.S. Cl. .......................................... 544/272; 544/263; 544/267; 544/273

[58] Field of Search ............................................. 544/272

[56] References Cited

U.S. PATENT DOCUMENTS 4,299,832 11/1981 Brown et al. ................ 544/267
5,068,236 11/1991 Suzuki et al. ................ 544/273

OTHER PUBLICATIONS

Linden et al., J. Med. Chem., 31, pp. 745–751; 1988.
Patel et al., Amer. Soc. Pharmcol. and Exptl. Therapeutics, Mol. Pharmacol., 33, 585–591, 1988.

*Primary Examiner*—Mukund J. Shah
*Assistant Examiner*—Pavanaram K. Sripada
*Attorney, Agent, or Firm*—Notaro & Michalos

[57] ABSTRACT

There are described 8-(1-aminocycloalkyl)-1,3-dialckylxantaine, their derivatives and their salts with adenosine antagonist activity. A process for the preparation of said compounds and pharmaceutical compositions containing them as antidepressant, nootropic and psychostimolant drugs are also described.

3 Claims, No Drawings

8-(1-AMINOCYCLOALKYL)-1,3-DIALKYLXANTHINE DERIVATIVES, PREPARATION PROCESS AND ANTIDEPRESSANT, NOOTROPIC AND PSYCHOSTIMULANT COMPOSITION THEREOFF

The present invention relates to 8-(1-aminocycloalkyl)-1,3-dialkylxanthine derivatives and their salts, that are active as selective antagonists of adenosine receptors; a process for their preparation, as well as pharmaceutical compositions containing them as active ingredients, which are therapeutically useful as antidepressant, nootropic and psychostimulant agents.

It is known that theophylline (1,3-dimethylxanthine) is capable of antagonizing the effects of adenosine by interacting with the receptors thereof, and that mainly to said properties its stimulating effects onto the central nervous system are to be ascribed. The lack of selectivity between the receptor subtypes A1 and A2, together with the relatively low affinity for said receptors, have imposed a severe limitation to the therapeutical use of this substance as an agent capable of enhancing the cognitive capacity, alertness and memory in man, because of the presence of pharmacologically relevant effects also onto the heart, kidney and smooth musculature. In European Patent Application n. 203,721 1,3-dialkyl-8-arylxanthine derivatives useful in the therapy of cardio-circulatory and intestinal apparatus conditions are described; document DE 3.843.117 relates to 1,3-dialkyl-8-cycloalkylxanthines therapeutically useful in the degenerative conditions that are typical of aging. With the present invention novel xanthine derivatives have been found, which selectively antagonize the adenosine A1 receptors and are surprisingly active onto the central nervous system as antidepressants, nootropa and psycostimulants at the same time; moreover they have low side-effects, which can not be ascribed to the adenosine A2-dependant receptors previously described. The present invention relates therefore to a compound of formula (I)

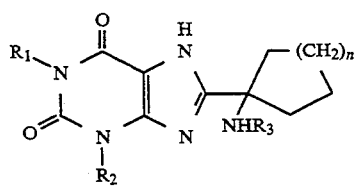

wherein

R1 and R2 stand for the same or different linear or branched (C1–C6)alkyl, linear or branched (C3–C4)alkenyl, linear or branched (C3–C4)alkinyl groups;

R3 is hydrogen; —COR4 in which R4 stands for a (C1–C6) alkyl, which is non-substituted or substituted with at least one group chosen from carboxyl and (C1–C6)alkyloxycarbonyl, phenyl, which is non-substituted or substituted with at least one group chosen from (C1–C4)alkoxy and hydroxy, (C1–C4) alkoxy, (C1–C4)alkylamine; —SO2R5 in which R5 is linear or branched (C1–C6)alkyl, phenyl, which is non-substituted or substituted with at least one (C1–C3)alkyl group;

n is from 1 to 2; and its salts.

In the present invention the compounds of formula (I) in which R1 and R2 are the same linear or branched (C1–C4)alkyl group, R3 is hydrogen and n is 1 are preferred. Especially preferred is a compound of formula (I) in which R1 and R2 are n-propyl, R3 is hydrogen and n is 1.

The compounds of formula (I) of the present invention can exist in a number of tautomeric forms, which forms, individually or in admixture, are all included in the above-mentioned formula (I), even though only one tautomeric form is represented for conveniency reasons. As the salts of the compounds of formula (I), there are included the acid addition salts that can be prepared in situ during the final isolation and the purification or by means of the separate reaction of the free base with the organic or inorganic acid, suitably chosen, for example, from hydrochloric, hydrobromic, phosphoric, metaphosphoric, nitric, sulphuric, tartaric, acetic, citric, malic, lactic, fumaric, benzoic, glycolic, gluconic, suffinic and p-toluenesulfonic acid. In the present invention also the base addition salts are included; they can be prepared as above thereby obtaining, e.g., ammonium, alkali metal and earth-alkali metal salts, such as the sodium, potassium and calcium salts, or salts formed with organic bases, such as di- or trialkylamines or alkanolamines, e.g. triethanolamine.

A further object of the present invention is the process for the preparation of the compounds of the general formula (I). The synthesis is carried out according to a scheme comprising the condensation of the compounds of formula (II)

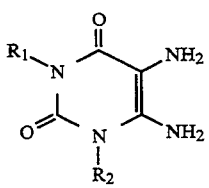

wherein R1 and R2 have the above-mentioned meanings, with a 1-aminocycloalkanecarboxylic acid derivative of formula (III)

In which n is from 1 to 2, R6 is a suitable protecting group for the amine function, especially trifluoroacetyl, and R7 is OH, OCOCF3, Cl.

Where R7 is OH, the reaction is carried out in the presence of a suitable condensing agent, such as a dialkyl carbodiimide or a dicycloalkyl carbodiimide, especially diisopropyl carbodiimide.

The condensation reaction gives rise to the formation of the compound of formula (IV)

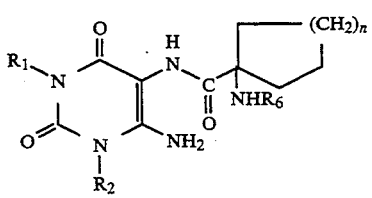

in which the substituents have the meanings described above. Said compound, after isolation and, if necessary, purification, is subjected to a cyclization reaction in the presence of a dehydrating agent, such as POCl3, in a suitable organic solvent, or under hydrolytic conditions, for example with 10% NaOH at the reflux temperature of the solution, thereby obtaining the compound of formula (V)

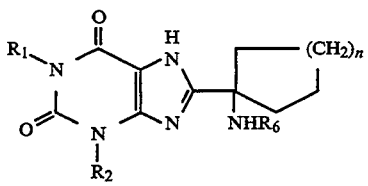

which can be subsequently deprotected to afford the compound of formula (I) in which R3 is hydrogen.

In a particularly preferred embodiment of the invention, said compound of formula (I) in which R3 is hydrogen can result directly from the hydrolytic cyclization reaction with concurrent deprotection of the exocyclic amine function. This occurs e.g. when R6 is trifluoroacetyl.

The compounds of the present invention with carboxyamide or sulfonamide functions in the position 1 of the cycloalkyl ring can be prepared according to procedures well known to a skilled mean by reacting the compound of formula (I) in which R3 is hydrogen with a suited activated derivative of acid R4CO2H, where R4 is alkyl optionally substituted by a suitably protected or masked terminal carboxyl group, or a phenyl possibly substituted by one or more alkoxy groups or by one or more hydroxy groups; or with a suitable derivative of acid R5SO3H in which R5 has the same meaning as described above. The formation of the compounds of the present invention with a carbamic or urethane function in the position 1 of the cycloalkyl ring can also be achieved by means of known procedures starting from the compound of formula (I) in which R3 is H, by reacting it with (C1-C4)alkyl chloroformate or (C1-C4)alkyl isocyanate, respectively.

The preparation of the compounds of formula (II), where they are not commercially available, can be carried out with methods described in literature (J.Org.Chem.16, 1879, (1951) and J.Am.Chem.Soc. 76, 2798 (1954)).

For the preparation of the compounds of formula (III), suitable protection reactions of the primary amine function will be on the contrary resorted to, said protection reactions being known to a person skilled in the art, starting from 1-aminocycloalkanecarboxylic acid; in a preferred embodiment of the present invention, said protection can be carried out by operating a trifluoroacetylation by means of trifluoroacetic anhydride.

As shown hereinafter in Examples 13 to 17, the compounds of formula (I) and their salts are selective antagonists of the adenosine A1 receptors, act onto the central nervous system as antidepressant, nootropa and psychostimulants at the same time and show low side effects ascribable to the A2 receptors. The compounds of formula (I) and their pharmaceutically acceptable salts of the present invention can therefore be advantageously used as the active ingredient for the preparation of therapeutically useful medicaments as antidepressants, nootropa and psychostimulants. Further possible indications are the degenerative conditions, such as senile dementia, Alzheimer's disease, cerebral organic syndrome, Parkinson's disease, traumatic damages to the central nervous system, post-neurological deficits, respiratory depression, neonatal cerebral damage.

Besides being employed as drugs acting onto the central nervous system, the compounds of present invention could also be used for the treatment of cardiac and respiratory disorders.

For said therapeutic uses, the compounds of the present invention or their pharmaceutically acceptable salts can be administered by the oral, topic, parenteral or rectal route in formulations containing them as the active ingredients at a therapeutically effective dosage with conventional, non-toxic pharmaceutical excipients. The term "parentheral", as used herein, includes subcutaneous, intravenous and intramuscular injections.

If the compounds of the present invention or pharmaceutically acceptable salts thereof, are in the form of a pharmaceutical composition, as in a preferred embodiment of the invention, the precise formulation employed will obviously depend on the chosen route of administration.

The pharmaceutical compositions suitable for the oral administration can be, e.g., tablets, aqueous or oily suspensions, dispersible powders or granules, hard or soft capsules, syrups or elixirs. The compositions for oral use can contain one or more sweltening, colouring, flavouring and preserving agents that are suited to provide elegant and palatable pharmaceutical compositions.

The formulations for oral use comprise tablets in which the active ingredient is mixed with non-toxic, pharmaceutically acceptable excipients. Said excipients can be inert diluents, such as calcium carbonate, sodium carbonate, lactose, calcium phosphate or sodium phosphate; granulating or disintegrating agents, such as wheat starch or alginic acid; binding agents such as starch or gelatins; lubricants, such as magnesium stearate, stearic acid or talcum.

The tablets can be non-coated or coated by means of the techniques conventionally known to a person skilled in the art, to the purpose of delaying the disintegration and absorption in the gastro-intestinal tract, thereby achieving a retard action with protracted liberation of the active ingredient.

The aqueous suspensions generally contain the active ingredients in admixture with suitable excipients. The excipients can be suspending agents, such as sodium carboxymethyl cellulose, methyl cellulose, hydroxypropyl methyl cellulose, sodium alginate, polyvinylpirrolidone; dispersing and wetting agents. They can also contain one or more preservatives, such as ethyl or -propyl p-hydroxybenzoate, one or more coloring agents; one or more flavouring agents, one or more sweltening agents.

The oily suspensions can also be formulated by suspending the active ingredient into a vegetal or mineral oil; they can contain sweltening and flavouring agents to make the preparation palatable.

The dispersible powders and granules that are suited for the preparation of an aqueous suspension by adding water contain the active ingredient in admixture with a dispersing or wetting agent, a suspending agent and one or more preserving agents.

The pharmaceutical composition of the present invention can also be in the form of a water/oil emulsion. The oil phase can consist of a vegetal or mineral oil. The emulsifying agents can be natural gums, such as acacia, or natural phosphatides, e.g. lecithins or ester compounds of natural or synthetic fatty acids. The syrups and elixirs can be formulated with sweltening agents, such as glycerol, sorbitol or sucrose.

The pharmaceutical compositions can be in the form of sterile injectable water or oil suspensions. The suspensions can be formulated according to the known techniques by using known dispersing or wetting agents and suspending agents. The sterile injectable preparation can be sterile injectable solutions or suspension in a solvent or diluent which is non-toxic and suitable for the parental use.

The compounds of the present invention or salts thereof can also be rectally administered in the form of suppositories. These compositions can be prepared blending the active ingredient with a suitable, non irritant excipient which is solid at room temperature but liquid at the rectal temperature: consequently it will melt in rectum and free the drug. Suitable excipients for this purpose are the polyethylene glycols and cocoa butter.

The therapeutically or prophylactically effective amount of a compound of the present invention, or salt thereof, depends on a number of factors including, e.g., the age and weight of the patient, the precise condition to be treated and its gravity, and the route of administration. However, an effective amount of the compound of the present invention for the treatment of troubles in the sphere of learning and memory will generally be within the range of 0.05-50 mg/kg of body weight per day, more frequently within the range of 0.5-5 mg/kg per day.

The examples that follow are to better demonstrate the present invention and they should not be taken as limiting anyway the scope of the present invention.

EXAMPLE 1

Preparation of 8-(1-aminocyclopentyl)-1,3-dipropylxanthine

A mixture of 11.4 g of 1-trifluoroacetylaminocyclopentanecarboxylic acid and 10.4 g of 5,6-diamino-1,3-dipropyluracil in 120 ml of methanol was treated with 8.7 ml of diisopropylcarbodiimide (DIPC). After 2 hours stirring at room temperature and 1 h at 4° C., the formed precipitate is filtered under vacuum, washed and dried, thereby obtaining 15.1 g of 6-amino-1,3-dipropyl-5-(1-trifluoroacetylamino cyclopentanecarboxamido)uracil m.p. 203°-4° C.

Said compound is then refluxed in 280 ml of 10% aqueous NaOH for 4 hours. After cooling down and neutralization (pH=6), the formed precipitate is filtered under vacuum, washed with water and dried, thereby obtaining 10.5 g of product which is finally purify by crystallization from ethanol.

m.p. (DSC)=195.6° C. (onset); IR (KBr): 3314 ($\nu$NH), 1698, 1650 cm$-1$($\nu$C=O); 1H-NMR (CDC13):$\delta$5.7 (3H,sb), 4.2-3.8 (4H,m), 2.5-1.5 (12H,m), 1.0 (6H,t); UV (EtOH): $\lambda$max=276 nm.

Elementary analysis for C16H25N5O2 (M.W. 319.41):

|       | C %   | H %  | N %   |
|-------|-------|------|-------|
| Calc. | 60.16 | 7.89 | 21.92 |
| Found | 59.97 | 8.09 | 22.48 |

EXAMPLE 2

Preparation of 8-(1-aminocyclopentyl)-1,3-dimethylxanthine

Starting from 1,3-dimethyl-5,6-diminouracil and following a procedure analogous to example 1, the title compound was prepared.

m.p.=288°-90° C.; IR (KBr): 1700, 1661 ($\nu$C=O), 1628 cm$-1$($\delta$NH);1H-NMR (CD3OD):$\delta$3,7(3H,s), 3.6(3H,s), 2.2-1.7 (8H,m); UV (EtOH): $\lambda$max=275 nm.

Elementary analysis for C12H17N5O2 (M.W. 263.30):

|       | C %   | H %  | N %   |
|-------|-------|------|-------|
| Calc. | 54.74 | 6.51 | 26.60 |
| Found | 54.39 | 6.80 | 26.35 |

EXAMPLE 3

Preparation of 8-(1-aminocyclopentyl)-1,3-diallylxanthine

Starting from 1,3-diallyl-5,6-diaminouracyl and following a procedure analogous to example 1, the title compound was prepared.

m.p. =186°-80° C.; IR (KBr): 1697, 1658 cm$-1$($\nu$C=O); 1H-NMR (CDC13):$\delta$6.0-5.6(2H,m),5-.2-5.0(4H,m), 4.5(4H,d), 2.2-1.7(8H,m); UV (EtOH):-$\lambda$max=279 nm.

Elementary analysis for C16H21N5O2 (M.W. 315.38):

|       | C %   | H %  | N %   |
|-------|-------|------|-------|
| Calc. | 60.93 | 6.71 | 22.21 |
| Found | 60.69 | 6.89 | 22.45 |

EXAMPLE 4

Preparation of 8-(1-aminocyclohexyl)-1,3-dipropylxanthine

Starting from 1-trifluoroacetylamino cyclohexanecarboxylic acid and following a procedure analogous to example 1, the title compound was prepared.

m.p.=172°-3° C.;IR(KBr):3319($\nu$NH), 1698, 1657($\nu$C=O),1612 cm$-1$($\nu$NH); 1H-NMR(CDC13):$\delta$5.2 (2H,sb), 4.2-3.8(4H,m),2-.2-1.5(14H,m), 0.95(6H,t); UV(EtOH):$\lambda$max=276 nm.

Elementary analysis for C17H27N5O2 (M.W. 333.44):

|       | C %   | H %  | N %   |
|-------|-------|------|-------|
| Calc. | 61.24 | 8.16 | 21.00 |
| Found | 61.08 | 8.38 | 20.89 |

EXAMPLE 5

Preparation of 8-(1-acetylaminocyclopentyl)-1,3-dipropylxanthine

To a suspension of 0.86 g of 8-(1-aminocyclopentyl)-1,3-dipropylxanthine in 8 ml of anhydrous tetrahydrofurane 0.3 ml of pyridine and 0.4 ml of acetyl chloride are added. The mixture is stirred for 2 hours at room temperature, followed by the addition of 1N HCl and extraction with ethyl acetate. The organic phase is washed with water, dried and evaporated to obtain 0.8 g of a raw product, which is eventually crystallized from isopropyl acetate.

m.p. (DSC)=132,2° C. (onset); IR (KBr): 1699, 1661, 1638 cm−1 ($\nu$C=O); 1H-NMR (CDCl3):$\delta$6.4 (1H,s), 4.2–3.8 (4H, m), 2.7–2.3 (4H,m), 2.2–1.5 (11H,m), 1.9 (6H,t); UV (EtOH): $\lambda$max=276 nm.

Elementary analysis for C18H27N5O3 (M.W. 361.45):

|       | C %   | H %  | N %   |
|-------|-------|------|-------|
| Calc. | 59.81 | 7.53 | 19.38 |
| Found | 59.67 | 7.38 | 19.31 |

EXAMPLE 6

Preparation of
8-(1-benzoylaminocyclopentyl)-1,3-dipropylxanthine

To a suspension of 4.3 g of 8-(1-aminocyclopentyl)-1,3-dipropylxanthine in 40 ml of anhydrous tetrahydrofurane 1.3 ml of pyridine and 1.9 ml of benzoyl chloride are added. The mixture is stirred for 2 hours at room temperature, followed by the addition of 1N HCl and extraction with ethyl acetate. The organic phase is washed with water, dried and evaporated to obtain 5.2 g of a raw product, which is eventually crystallized from isopropyl acetate.

m.p. (DSC)=199,2° C.(onset); IR (KBr): 3349 ($\nu$NH), 1697, 1656 cm−1 (84 C=O); 1H-NMR (CDCl3): $\delta$ 7.8–7.6 (2H,m), 7.5–7.2 (3H,m), 6.6 (1H, s), 4.2–3.8 (4H, m), 2.7–2.3 (4H,m), 2.2–1.5(8H,m), 1.9(6H,t); UV(EtOH):$\lambda$max=277 nm.

Elementary analysis for C23H29N5O3 (M.W. 423.52):

|       | C %   | H %  | N %   |
|-------|-------|------|-------|
| Calc. | 65.23 | 6.90 | 16.54 |
| Found | 65.27 | 7.07 | 16.77 |

EXAMPLE 7

Preparation of
1,3-dipropyl-8-(1-(3,4,5-trimethoxybenzoylamino)cyclopentyl)xanthine Starting from 3,4,5-trimethoxyenzoyl chloride and following a procedure analogous to example 6, the title compound was prepared.

m.p.=(DSC)=98.7 C (onset); IR (KBr): 1704, 1663, 1624 cm−1($\nu$C=O); 1H-NMR(CDCl3/CD3OD):$\delta$7,2 (2H,s), 4.2–3.8 (4H,m),3.9(6H,s),3.8(3H,s), 2.7–2.3 (4H,m), 2.2–1.5(8H,m),1.9(6H,t);UV(EtOH):-$\lambda$max=273 nm.

Elementary analysis for C26H35N5O6 (P.M. 513.595):

|       | C %   | H %  | N %   |
|-------|-------|------|-------|
| Calc. | 60.80 | 6.87 | 13.64 |
| Found | 60.49 | 7.02 | 13.40 |

EXAMPLE 8

Preparation of
1,3-dipropyl-8-(1-methanesulfonylaminocyclopenthyl)xanthine

To a suspension of 4.2 g of 8-(1-aminocyclopentyl)-1,3-dipropylxanthine in 40 ml of anhydrous tetrahydrofurane 1.7 ml of pyridine and 1.7 ml of methanesulfonyl chloride are added. The mixture is stirred for 4 hours at room temperature, followed by the addition of 1N HCl and extraction with ethyl acetate. The organic phase is washed with water, dried and evaporated to obtain 2.3 g of raw product, which is finally purified by chromatography on SiO2 and crystallized from ethanol-water.

m.p. (DSC)=144.1° C. (onset); IR (KBr): 1697,1659($\nu$C=O),1155 cm−1($\nu$SO2); 1H-NMR (CDCl3):$\delta$6.3(1H,s), 4.2–3.8(4H,m),2.8(3H,s), 2.5–2.2(4H,m), 2.2–1.5 (8H,m), 1.0 (6H,t); UV (EtOH):-$\lambda$max=277 nm.

Elementary analysis for C17H27N5O4S (M.W. 397.49):

|       | C %   | H %  | N %   |
|-------|-------|------|-------|
| Calc. | 51.37 | 6.85 | 17.62 |
| Found | 51.34 | 7.02 | 18.01 |

EXAMPLE 9

Preparation of
1,3-dipropyl-8-(1-p-toluenesulphonylamino cyclopentyl)xanthine

To a suspension of 200 mg of 8-(1-aminocyclopentyl)-1,3-dipropylxanthine in 1.5 ml of dimethylformamide 0.18 ml of pyridine and 190 mg of p-toluene sulfonyl chloride are added. The mixture is stirred for 2 hours at room temperature, followed by the addition of 1N HCl. The precipitate thereby obtained is filtered under vacuum, washed and dried, thereby obtaining 45 mg of a product.

m.p.=208–211 C; IR (KBr): 1701, 1649 ($\nu$C=O), 1162 cm−1 ($\nu$s SO2); 1H-NMR (CDCl3): $\delta$ 7.5 (2H,d),7.0(2H,d),6.5(1H,s),4.0(4H,t),2.5–2.1 (4H, m), 2.2 (3H, s), 2.1–1.5 (8H, m), 1.0 (6H,t); UV (EtOH): $\lambda$max=277 nm.

Elementary analysis for C23H31N5O4S (M.W. 473.59):

|       | C %   | H %  | N %   |
|-------|-------|------|-------|
| Calc. | 58.33 | 6.60 | 14.79 |
| Found | 57.98 | 6.50 | 14.46 |

EXAMPLE 10

Preparation of
1,3-dipropyl-8-(1(N-ethoxycarbonylamino)cyclopentyl)xanthine

To a suspension of 4.5 g of 8-(1-aminocyclopentyl)-1,3-dipropylxanthine in 45 ml of anhydrous tetrahydrofurane 1.83 ml of pyridine and 1.97 ml of ethyl chloroformiate are added. The mixture is stirred for 2 hours at room temperature, followed by the addition of 1N HCl and extraction with ethyl acetate. The organic phase is washed with water, dried and evaporated to obtain 4.2 g of raw product, which is finally crystallized from ethanol/water.

m.p. (DSC)=158,4° C. (onset); IR(KBr):1712,1685,1643 cm−1(νC=O); 1H-NMR(CDC13): δ5.4 (1H,s), 4.3–3.8(6H,m),2-.5–2.1(4H,m),2.1–1.5(8H,m), 1.3–0.8 (9H, m); UV-(EtOH):λmax=277 nm.

Elementary analysis for C19H29N5O4 (M.W. 391.47):

|  | C % | H % | N % |
|---|---|---|---|
| Calc. | 58.30 | 7.47 | 17.89 |
| Found | 58.55 | 7.64 | 18.04 |

EXAMPLE 11

Preparation of 1,3-dipropyl-8-(1(N'-propylureido)cyclopentyl)xanthine

A suspension of 100 mg of 8-(1-aminocyclopentyl)-1,3-dipropylxanthine in 10 ml of anydrous tetrahydrofurane was treated with 0.05 ml of n-propyl isocyanate. The mixture is stirred for 18 hours at room temperature, followed by evaporation under vacuum, thereby obtaining 124 mg of product.

m.p.=198°–200° C. IR (KBr):1706,1655,1635 cm−1(νC=O); 1H-NMR(CDC13/CD3OD): δ3,9(4H,t),3,0(2H,t),2,4–2,1(4H,m),2,1–1,4(10H,m), 1,0 (6H,t); UV (EtOH):λmax=277 nm.

Elementary analysis for C19H27N5O5 (M.W. 405.455):

|  | C % | H % | N % |
|---|---|---|---|
| Calc. | 59.38 | 7.97 | 20.78 |
| Found | 59.15 | 8.09 | 20.59 |

EXAMPLE 12

Preparation of 1,3-dipropyl-8-(1-emimalonamido cyclopentyl)xanthine

To a suspension of 4.5 g di 8-(1-aminocyclopentyl)-1,3-dipropylxanthine in 45 ml of anhydrous tetrahydrofurane, 1.4 ml of pyridine are added and, after cooling to 5° C., 2.26 ml of ethyl malonyl chloride are dropwise added. The mixture is stirred at room temperature for 2 hours, followed by concentration under vacuum, addition of 1N HCl and extraction with ethyl acetate. The organic phase is washed with water, dried and evaporated, thereby obtaining 6.5 g of raw product which is purified by column chromatography (SiO2). 2.6 g of mono malonamide mono ethyl ester are obtained, which is finally saponified by treatment with tetrahydrofurane (26 ml) and NaOH 1N (30 ml) at room temperature for 1 hour.

The reaction mixture is concentrated under vacuum and made acidic with 2N HCl, thereby obtaining the precipitation of the product which is filtered under vacuum, washed with water and dried. 2.33 g of a white solid are obtained, which is finally recrystallized from ethanol/water.

m.p. (DSC)=195,6° C. (onset); IR (KBr): 1731, 1704, 1665, 1633 cm−1(νC=O); 1H-NMR (CDC13): δ4,0(4H,t), 3,6(2H,s), (2,5–2,1(4H,m), 2,1–1,5 (8H,m), 0,9 (6H,t); UV (EtOH): λmax=277 nm.

Elementary analysis for C19H27N5O5 (M.W. 405.455):

|  | C % | H % | N % |
|---|---|---|---|
| Calc. | 56.28 | 6.71 | 17.27 |
| Found | 56.48 | 6.58 | 17.07 |

EXAMPLE 13

Binding to the adenosine receptors

The receptor binding tests were carried out on preparations of sinaptosomial membranes from rat brain.

Binding to the A1 receptors has been carried out as follows:

200 μg of membrane proteins were incubated for 1 h at 25° C. with the test substance and 0.3 nM (3H)-DPCPX in 400 μl of 50 mM tris-HCl pH=7.4. The non-specific binding was determined with 20 μM R-PIA. The binding to the A2 receptors was carried out by incubating 200 μg of membrane proteins for 1 h at 25° C. with the test substance, 4 nM (3H)-NECA and 50 nM CPA. The non-specific binding was determined with 200 μM CPA.

The incubations were blocked by centrifugal methods and the separation of the bound from free material was carried out, followed by determination of the contained radioactivity by liquid scintillation. The dosis-inhibition curves were obtained by assaying the receptor displacement at 14 different concentrations of the test substance (all the tests are carried out in triplicate). The tested substances were dissolved into dimethylsulfoxide and diluted in 50 mM Tris-HCl, buffer pH=7.4. The IC50 values were determined by means of non-linear regression curves and transformed into Ki values according to the Cheng-Prusoff equation.

TABLE 1

Affinity to the adenosine receptors

| SUBSTANCE | Ki,A1(nM) | Ki,A2(nM) | SELECTIVITY (A2/A1) |
|---|---|---|---|
| COMPOUND EX. 1 | 26 | 54615 | 2100 |
| COMPOUND EX. 6 | 115 |  |  |
| COMPOUND EX. 8 | 166 |  |  |
| COMPOUND EX. 10 | 108 |  |  |
| COMPOUND EX. 12 | 6992 |  |  |

EXAMPLE 14

Antidepressant activity: "Behavioral despair" test

The test described in R. D. Porsolt et al., Arch.Int.-Pharmacodyn. 229, 327 (1977), which allows the antidepressant activity of a drug to be evaluated on an animal placed in an unusual, stress-causing environment, such as the water environment, was carried out. White male CD 1 (Charles River) mice weighing 24–35 g were used.

1 h before the immersion in water, the animal is administered the test compound by the intraperitoneal (i.p.) route. The period the animal stay in water is 6': from the 2nd to the 6the minute, the time lengths during which the animal remains motionless is measured (motionlessness is the symptom through which depression is revealed). Table II shows the results obtained with some compounds of the invention, as percent variation of the motionlessness period length of the treated animals relative to the control group. As the reference substances the xanthines theophylline and caffeine, the nootropically acting drug oxiracetam and the tricyclic antidepressant desipramine were included.

TABLE II

| SUBSTANCE | DOSE (mg/kg) | % VARIATION OF MOTIONLESSNESS TIME LENGTH |
|---|---|---|
| COMPOUND EX. 1 | 10 | −28.33 |
| COMPOUND EX. 1 | 20 | −42.93 |
| COMPOUND EX. 6 | 10 | −24.22 |
| THEOPHYLLINE | 18.7 (os) | −48.88 |
| CAFFEINE | 25 (os) | −30.34 |
| OXIRACETAM | 500 | −29.07 |
| DESIPRAMINE | 15 | −24.50 |

EXAMPLE 15

Antidepressant activity: antagonism to reserpine

There was performed the test described in M.Bourin et al., Arzneim.-Forsch./Drug Res. 33(II), 1173 (1983), that allows antidepressant activity of a drug to be assayed as a function of the antagonism it exerts to hypothermia induced by reserpine. Male white CD 1 (Charles River) mices weighing 23-35 g were used.

Before every test, the basal rectal temperature of every mouse is registered. The test substances are administered by the intraperitoneal (i.p.) route 4 hours after the intraperitoneal administration of reserpine (2.5 mg/kg). The rectal temperature is measured again at t=O and 30', 60', 90' and 120' after administration of the drug. Table III is the record of the maximum temperature variations relative to t=O on the animals treated with the compound of example 1, desipramine, nortriptyline, theophylline and caffeine.

TABLE III

| SUBSTANCE | DOSE (mg/kg) | Δ TEMPERATURE (°C.) |
|---|---|---|
| COMPOUND EX. 1 | 10 | +0.26 |
| COMPOUND EX. 1 | 20 | +0.71 |
| DESIPRAMINE | 16 | +1.39 |
| NORTRIPTYLINE | 10 | +2.34 |
| THEOPHYLINE | 20 | +0.81 |
| CAFFEINE | 20 | +1.63 |

EXAMPLE 16

Nootropic activity: "Passive avoidance" test

The test described in R.Verloes et al., Psychopharmacology 95, 226, (1988), which allows the antiamnesia effects of new drugs to be evaluated as a function of their ability of antagonizing amnesia induced by scopolamine, was performed. White male CD 1 (Charles River) mice weighing 25-35 g were used.

The animal is introduced for a first time into a cage comprising a lighted sector and a dark sector which are connected by a door. After opening the door, the mouse from the lighted sector enters the dark one, where it receives a 70 V electric shock lasting 5 sec (acquisition trial). 24 hours later, the test is repeated in the same conditions (retention trial), the lack of passage to the dug sector within the first 3' from opening-door being registered. A second group of animals is administered scopolamine intraperitoneally at the dosis of 2 mg/kg 30' before the acquisition trial. The substances to be tested are administered, also by the intraperitoneal route, to a third group 1 hour before acquisition trial and 30' before the scopolamine administration. Table IV shows the antiamnesia activity of the compound of example 1 and some reference substances, as the percentage of animals that do not trespass the door within the first 30' in the group treated with scopolamine+test compound.

TABLE IV

| SUBSTANCE | DOSE | ANTIAMNESIC ACTIVITY |
|---|---|---|
| COMPOUND EX. 1 | 10 | 80% |
| CAFFEINE | 10 | 60% |
| THEOPHYLINE | 20 | 30% |
| 8-PHENYLTHEOPHYLINE | 10 | 40% |
| DESIPRAMINE | 45 | 30% |
| OXIRACETAM | 1000 (os) | 40% |

EXAMPLE 17

Locomotor activity: "Activity cage" test

This test allows the spontaneous locomotor activity of the animal to be studied. Male Wistar (Charles River) rats weighing 150-250 g were used.

30' before being admitted to the activity cage, the animals are treated intraperitoneally with the test substance. The printer connected to the system records the number of movements performed by the rats within the first 5' from the moment they enter the cage. Table V shows the ED50 values relative to the % increase of spontaneous motion activity of the treated animal relative to the control group.

TABLE V

| SUBSTANCE | DE$_{50}$ (mg/kg) | 95% CONFIDENCE LIMIT |
|---|---|---|
| COMPOUND EX. 1 | 0.492 | 0.480–0.504 |
| CAFFEINE | 4.333 | 4.024–4.643 |
| 8-PHENYLTHEOPHYLINE | 6.011 | 4.197–7.825 |
| THEOPHYLINE | ~3.75 | |

We claim:
1. A compound of formula (I)

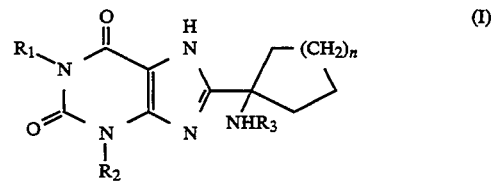

characterized in that
R1 and R2 stand for the same or different linear or branched (C1–C6)alkyl, linear or branched (C3-C4)alkenyl, linear or branched (C3–C4)alkinyl groups;
R3 is hydrogen; —COR4 in which R4 stands for a (C1–C6) alkyl, which is non-substituted or substituted with at least one group chosen from carboxyl and (C1–C6)alkyloxycarbonyl, phenyl, which is non-substituted or substituted with at least one group chosen from (C1–C4)alkoxy and hydroxy, (C1–C4) alkoxy, (C1–C4)alkylamine; —SO2R5 in which R5 is linear or branched (C1–C6)alkyl, phenyl, which is non-substituted or substituted with at least one (C1–C3)alkyl group;
n is from 1 to 2; and its salts.
2. A compound as claimed in claim 1, characterized in that R1 and R2 are the same linear or branched (C1–C4)alkyl group, R3 is hydrogen and n is 1.
3. A compound as claimed in claim 1, characterized in that R1 and R2 are n-propyl, R3 is hydrogen and n is 1.

* * * * *

REEXAMINATION CERTIFICATE (3679th)

United States Patent [19]

Brufani et al.

[11] B1 5,378,844

[45] Certificate Issued Dec. 1, 1998

[54] 8-(1-AMINOCYCLOALKYL)-1,3-DIALKYLXANTHINE DERIVATIVES, PREPARATION PROCESS AND ANTIDEPRESSANT, NOOTROPIC AND PSYCHOSTIMULANT COMPOSITION THEREOF

[75] Inventors: Mario Brufani, Rome; Romolo Scuri, Piacenza; Stefano Ceccarelli, Frosinone; Patrizia DeVellis, Frosinone; Patrizia Giannetti, Frosinone; Agnese Paesano, Frosinone; Zanarella Sergio, Mentana, all of Italy

[73] Assignee: Biomedica Foscama Industria, Rome, Italy

Reexamination Request:
No. 90/004,841, Nov. 14, 1997

Reexamination Certificate for:
Patent No.: 5,378,844
Issued: Jan. 3, 1995
Appl. No.: 7,757
Filed: Jan. 22, 1993

[30] Foreign Application Priority Data

Jan. 24, 1992 [IT] Italy .................... MI91A0132

[51] Int. Cl.$^6$ .................................. C07D 473/08
[52] U.S. Cl. .................. 544/272; 544/263; 544/267; 544/273
[58] Field of Search .................................. 544/272

[56] References Cited

U.S. PATENT DOCUMENTS 5,641,784   6/1997   Küfner-Mühl et al. ............ 514/263

FOREIGN PATENT DOCUMENTS

WO92/00297   1/1992   WIPO.

Primary Examiner—Mukund J. Shah

[57] ABSTRACT

There are described 8-(1-aminocycloalkyl)-1,3-dialckylxantaine, their derivatives and their salts with adenosine antagonist activity. A process for the preparation of said compounds and pharmaceutical compositions containing them as antidepressant, nootropic and psychostimolant drugs are also described.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–3 is confirmed.

* * * * *